United States Patent [19]

Cush

[11] Patent Number: 5,255,075
[45] Date of Patent: Oct. 19, 1993

[54] OPTICAL SENSOR

[75] Inventor: Rosemary Cush, Northampton, England

[73] Assignee: GEC-Marconi Limited, Stanmore, England

[21] Appl. No.: 845,662

[22] Filed: Mar. 4, 1992

[30] Foreign Application Priority Data

Mar. 22, 1991 [GB] United Kingdom ............... 9106102

[51] Int. Cl.$^5$ .......................................... G01N 21/75
[52] U.S. Cl. .................................. 356/445; 356/128; 356/352
[58] Field of Search ........................ 356/128, 352, 445

[56] References Cited

FOREIGN PATENT DOCUMENTS 2174802 11/1986 United Kingdom .

OTHER PUBLICATIONS

Harrick, N. J., "Internal Reflection Spectroscopy", John Wiley and Sons, pp. 147-177, (1967).
Dahne, C. et al, "Detection of Antibody-Antigen Reactions At A Glass Liquid Interface: A Novel Fibre-Optic Concept", Proc. SPIE, vol. 514, pp. 75-79 (1984).
Daniels, P. B. et al, "Surface Plasmon Resonance Applied To Immunosensing", Sensors and Actuators, 15, pp. 11-18 (The Netherlands, 1987).
Liedberg, B. et al, "Surface Plasmon Resonance For Gas Detection and Biosensing", Sensors and Actuators, 4, pp. 299-304, (The Netherlands, 1983).
Nellen, P. M. et al, "Integrated Optical Input Grating Couplers As Biochemical Sensors", Sensors and Actuators, 15, pp. 285-295 (1988).
Hardy, E. E. et al, "Coated Optical Guides For Spectrophotometry Of Chemical Reactions", Nature, vol. 257, pp. 666-667 (Oct., 1975).
Flanagan, M. T. and Pantell, R. H., "Surface Plasmon Resonance Sensors and Immunosensors", Electron, Letts. 8th, vol. 20, No. 23, pp. 968-970 (1984).

Primary Examiner—Richard A. Rosenberger
Attorney, Agent, or Firm—Jacobson, Price, Holman & Stern

[57] ABSTRACT

This invention relates to an optical sensor for testing a biochemical sample. The sensor includes a resonant mirror device 1 and a prism 2 disposed adjacent the device 1 for coupling an input beam of light to the device 1. The input beam of light having a comb spectrum with a uniform spacing between adjacent lines or bands of the spectrum is produced by a comb spectrum source 10. The comb spectrum may be produced by a diode laser with multiple longitudinal modes. The input beam of light is polarized by a polarizer 4 to provide equal TE and TM components. The resonant mirror device is arranged in the paths of said input beam of light such that resonance is excited for at least one of said components, An analyser 11 is arranged to receive said components of the beam of light reflected from the device 1 for producing an output beam having a spectrum including a series of bright and/or dark lines or bands corresponding to the lines or bands of the comb spectrum of the input beam. When a sensing layer of the resonant mirror device is sensitized by the chemical sample, an angular shift in the resonance angle takes place and this causes the lines or bands of the output spectrum to be swept across a reference point where detector means 12 is located to count the number of lines or bands swept across the reference point. The angular shift in the resonance angle is equal to the product of the distance between adjacent lines of the comb spectrum and the number of lines swept across the reference point.

27 Claims, 4 Drawing Sheets

OPTICAL SENSOR

The invention relates to an improvement in or relating to an optical sensor and a method of testing a chemical sample.

GB-A No. 2174802 discloses a Resonant Mirror Sensor which can be used for detecting the presence of analytes in a test sample by measuring changes in the optical properties of a sensing layer, which is immobilized within the evanescent field at the surface of the device. This layer may be, for example, a layer of antibodies, where binding of a specific analyte to the antibody results in a change in the thickness and refractive index of the sensing layer. The change in the sensing layer is monitored by measuring its effect on the angle of resonance of the resonant mirror structure. The angle at which resonance occurs is in turn measured by monitoring the phase of light reflected from the device. When the incident angle is equal to the resonant angle, the phase of the reflected light undergoes a change of $2\pi$ radians, and the angle at which this phase change occurs varies as the sensing layer changes. This is a very sensitive measuring technique, capable of detecting thickness variations in the sensing layer of a few Å.

A number of techniques are used to measure the phase change in the reflected beam. The main technique used is to utilise monomode light and to make use of the fact that light polarized perpendicularly to the plane of incidence (TE polarized) undergoes resonance at a different angle to the orthogonal component (TM polarized). An optical sensor incorporating this technique is disclosed in GB Patent Application No. 9020965.1. A part of the incident light is launched into each polarization direction, and the two components are made to interfere at the output. The phase difference between the two components is measured and, by using a compensator to remove the background phase difference, the phase difference is made to be zero away from the resonance and at a maximum of radians on resonance. This results in an intensity variation in the output beam, which is maximum away from the resonance and drops to zero at the resonant angles. By rotating the analyser by $\pi/2$ radians, a phase shift of $\pi$ is added to one component, resulting in the output beam intensity being zero away from resonance and maximum on resonance.

The sensor may be used with a collimated beam (rotating the prism to vary the incident angle) or with a focused or wedge beam as disclosed in GB Application No. 9020965.1. In the latter case the projected output beam is of the form of two black lines, corresponding to the resonances, on a bright background (or alternatively, two bright bands on a dark background. The positions of these resonances are measured using a detector array, for example, a CCD array. Although it would be possible to measure small peak shifts using a single detector, the initial angular position will vary from sample to sample, and so detectors are required over the full range over which a resonance may occur.

The use of detector arrays results in a large number of data points being analysed in order to determine the position of the peak, so requiring complex processing. Whilst this is necessary when dealing with small angle shifts, for larger angle shifts an alternative, simpler technique may be used which utilizes the wavelength dependent properties of the resonant mirror sensor.

According to the invention there is provided a method of testing a biochemical sample, the method comprising providing an optical evanescent wave sensor device having a dielectric cavity and a sensing layer, providing an input beam of light having a comb spectrum with a uniform spacing between adjacent lines or bands of the spectrum, coupling said beam of light to said device to excite resonance in said device and projecting light reflected from said device onto an analyser for producing an output beam of light having a spectrum of a series of bright and/or dark lines or bands corresponding to the lines or bands, of the comb spectrum of the input beam of light, sensitizing the sensing layer by the test sample, thereby causing an angular shift in the resonance angle, said lines or bands in the output spectrum being swept across a reference point as a result of said angular shift in the resonance angle and counting said lines or bands swept across said reference point, said angular shift in the resonance angle being equal to the product of the counted number of lines or bands swept across the reference point and the distance between two adjacent lines or bands in the output spectrum.

Further according to the invention there is provided an optical sensor for testing a biochemical sample, said sensor comprising means for providing an input beam of light having comb spectrum with a uniform spacing between adjacent lines or bands of the spectrum, an optical evanescent wave sensor device having a dielectric cavity and a sensing layer, means for coupling said beaus of light to said sensor device and projecting light reflected from said device onto an analyser for producing an output beam of light having a spectrum of a series of bright and/or dark lines or bands corresponding to the lines or bands of the comb spectrum of the input beam, said sensing layer being sensitized by the test sample, when the optical sensor is in use, thereby causing an angular shift in the resonance angle, said lines or bands in the output spectrum being swept across a reference point as a result of said angular shift in the resonance angle and means for counting said lines or bands swept across said reference point.

Preferably the input beam of light has coherent TE and TM components and said device is arranged in the path of said input beam of light such that one of said components excites resonance in said device. The device may be arranged in the path of the input beam of light such that resonance is excited for both of said TE and TM components.

By TE component is meant a component whose electric vector is perpendicular to the plane of incidence of the beam of light and by TM component is meant a component whose electric vector is in the plane of incidence of the beam of light.

The sensor device may be a resonant mirror device arranged in combination with coupling means for coupling light into said device. The resonant mirror device which may be used in the optical sensor embodying the invention is simple in construction, consisting of a prism structure onto which one low and one high index dielectric film is deposited. These form a resonant cavity on the totally internally reflecting face of the prism. Antibodies for the species to be detected are immobilized onto this surface. Light is reflected off this surface within the prism and the phase of the reflected light is monitored. As the detected species binds to the antibody layer the angle at which resonance occurs changes, and this can be detected as a measure of the concentration of the detected species in the test sample.

Preferably the input beam having comb spectrum is produced by a diode laser with multiple longitudinal modes. Alternatively a broad band source such as a light emitting diode may be used in conjunction with a Fabry-Perot or Mach-Zehnder interferometer.

Preferably the input beam of light is linearly polarized with TE and TM components by a polarizer arranged in the path of the beam of light.

The polarizer may be arranged at 45° to the TE and TM transmission axes for providing equal components of TE and TM light and the analyser may be arranged at 90° to the polarizer for providing a series of bright lines and bands in the output spectrum.

The output optics for the reflected light may include a compensator disposed adjacent said analyser to remove any phase difference which is introduced between the TE and TM components on total internal reflection and by birefringence in the device.

Preferably a detector is disposed at the reference point for detecting the lines or bands swept across the reference point.

Further an array of detectors may be disposed in the path of said output beam to count lines or bands swept across two or more than two reference points.

The invention will now be described further by way of example with reference to the accompanying drawing in which.

Figure 1:
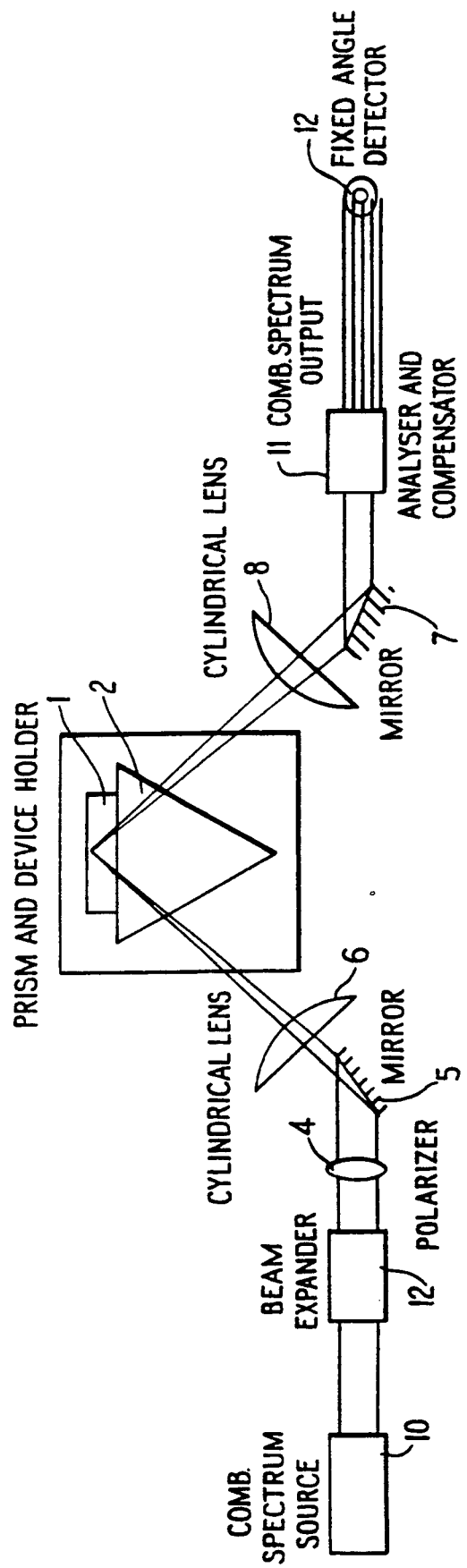
FIG. 1 illustrates an optical sensor according to the invention for use with a resonant mirror device.
Figure 2:
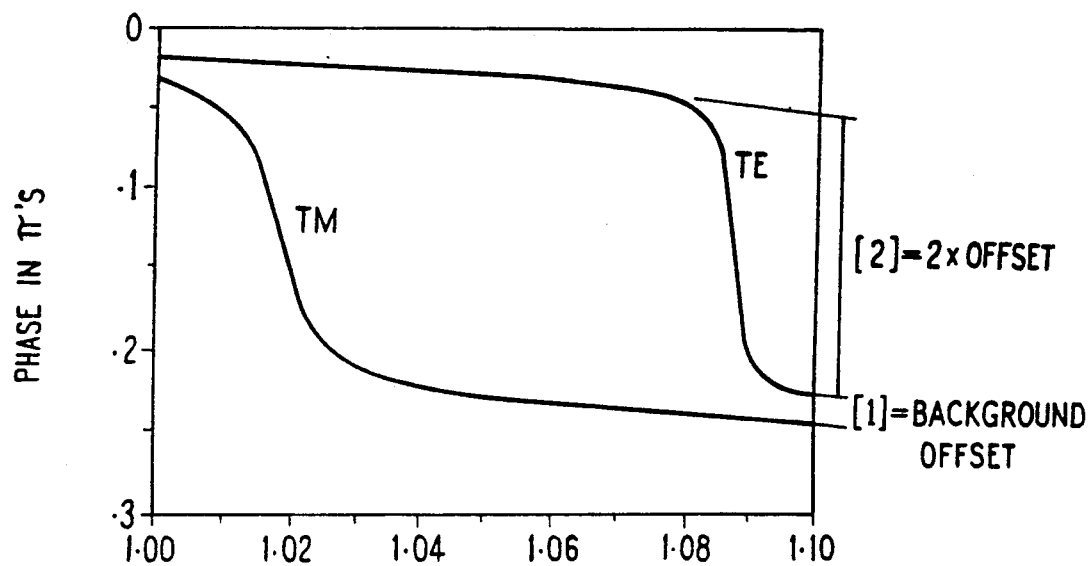
FIG. 2 is a graph of a phase shift on reflection versus angle for TE and TM reflected waves, note that the steps (2) associated with the resonances are both of $2\pi$ height, and that there is, or may be, a small offset (1) which is corrected by the compensator.
Figure 4:
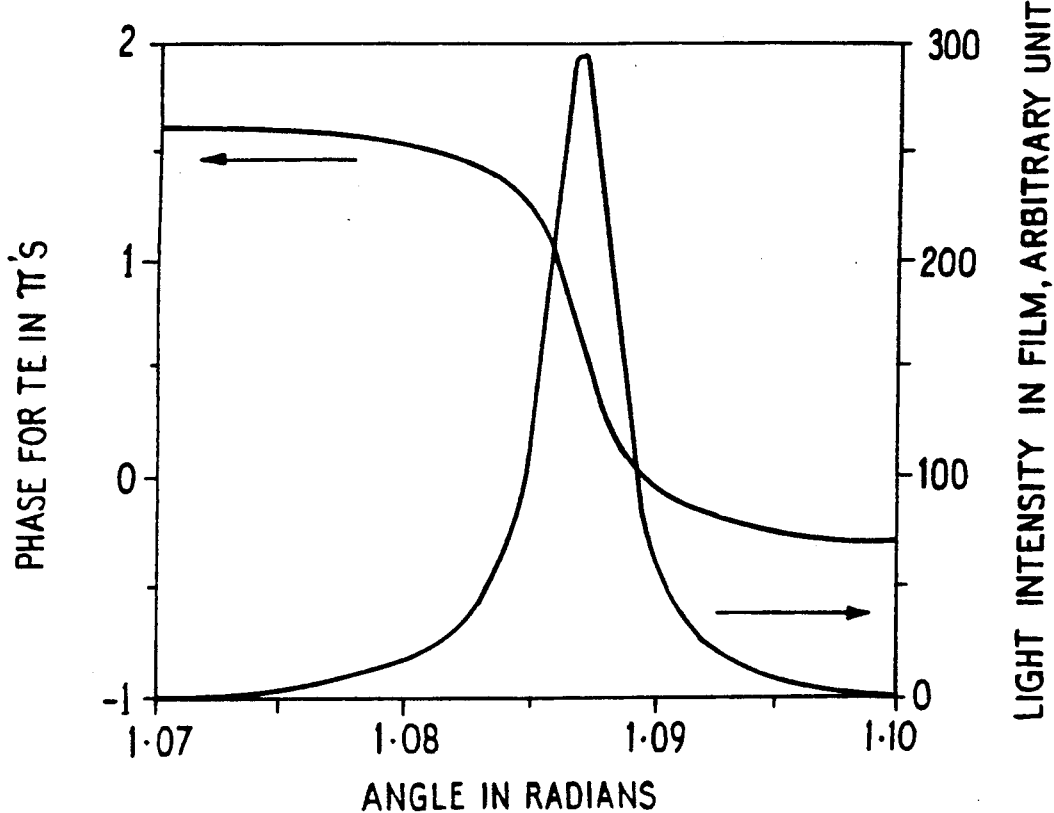
Figure 6:
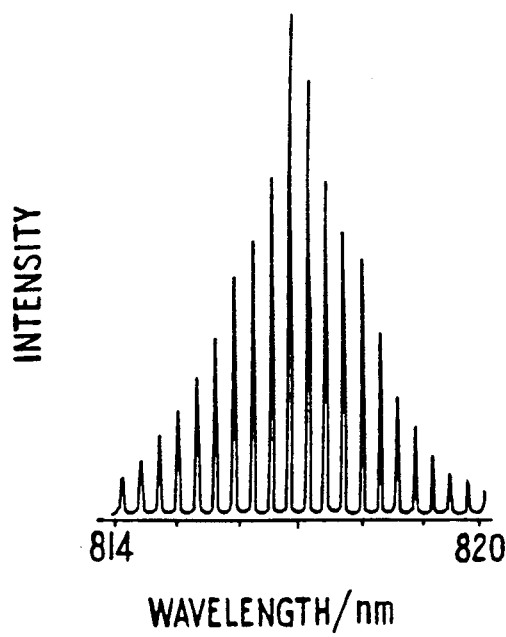
Figure 5A:
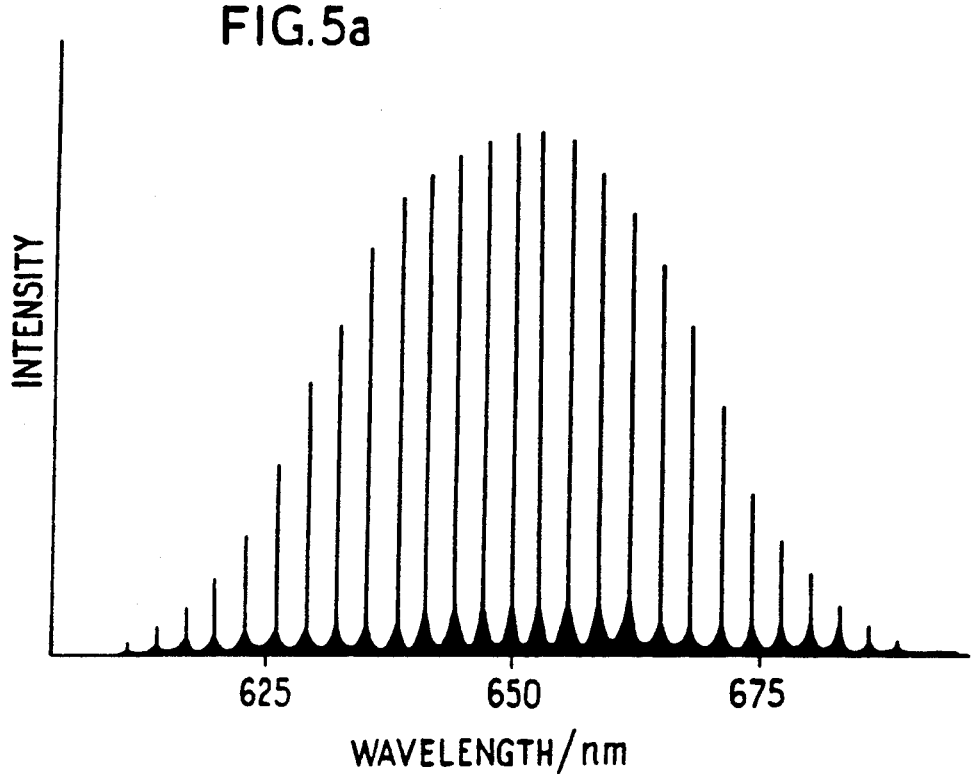
Figure 5B:
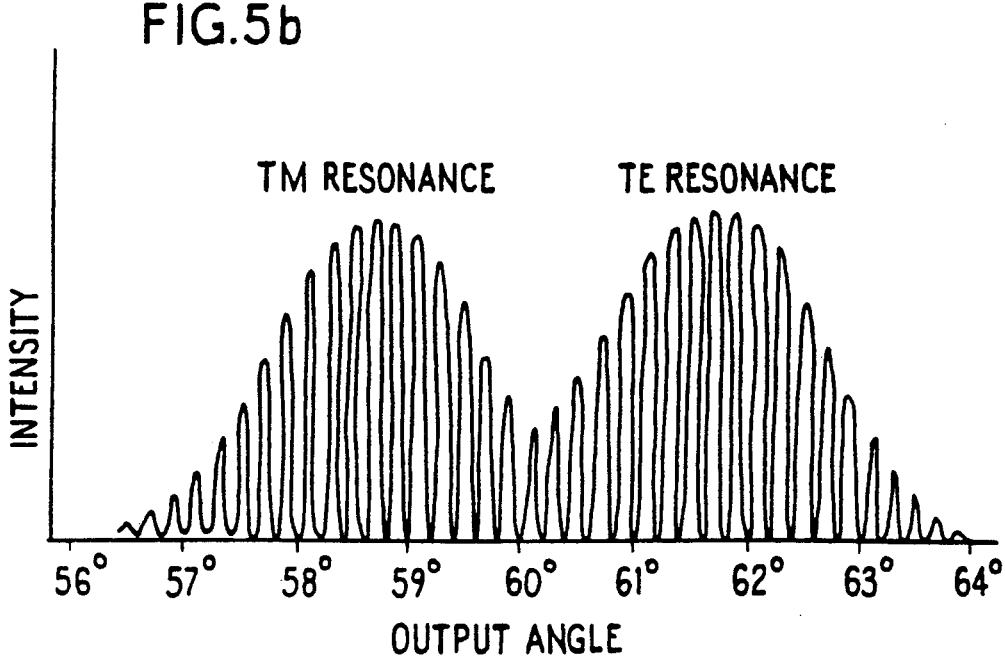

FIG. 4 is a double plot showing the phase v angle for TE component as in FIG. 2, and the corresponding light intensity in the sensed film. This shows that the width of the phase step and the width of the resonance are the same. Arrows indicate the relevant ordinate for each graph;

FIG. 5a illustrates a comb spectrum of an input beam and FIG. 5b illustrates an output intensity profile corresponding to the input spectrum of FIG. 5a; and FIG. 6 illustrates a longitudinal mode spectrum of a diode laser.

Referring to the drawings, the resonant mirror device and the coupling device disposed adjacent thereto are mounted on a rotatable platform. The coupling device is a prism 2 as shown in the drawing. The prism 2 couples light into the device at an angle of incidence depending on the angular position of the rotatable platform relative to the beam of light.

The input optics, provides a wedge beam of light allowing a range of input angles of incidence to be monitored. The input beam of light is produced by a comb spectrum source 10. A number of different sources may be used with the sensor to provide the comb spectrum. For example the source may be a diode laser with multiple longitudinal modes, as shown in FIG. 6. Alternatively, a broadband source, such as a light emitting diode (LED), may be used in conjunction with a Fabry-Perot or Mach-Zehnder interferometer. The requirement in all cases is that the spectral line spacing is greater than the spectral width of the device resonance. This is given, for narrow linewidths, by:

$$\Delta\lambda = \frac{\lambda n \cos\theta \Delta\theta}{(\partial K_R / \partial k)}$$

where is the center wavelength, $k = 2\pi/\lambda$, is the incident angle in the substrate, n is the refractive index of the prism and $\partial K_R/\partial k$ is the dispersion of the resonance wavevector of the resonant mirror device at the center wavelength.

The input beam of light is passed on to a polarizer 4 through a beam expander 12. The polarizer is arranged to produce a linearly polarized light with two components transverse electric (TE) and transverse magnetic (TM). The polarizer is set at 45° to the TE and TM transmission axes and thus provides equal components of TE and TM light. TE component undergoes a phase change on reflection which is different compared with TM component.

Figure 3:
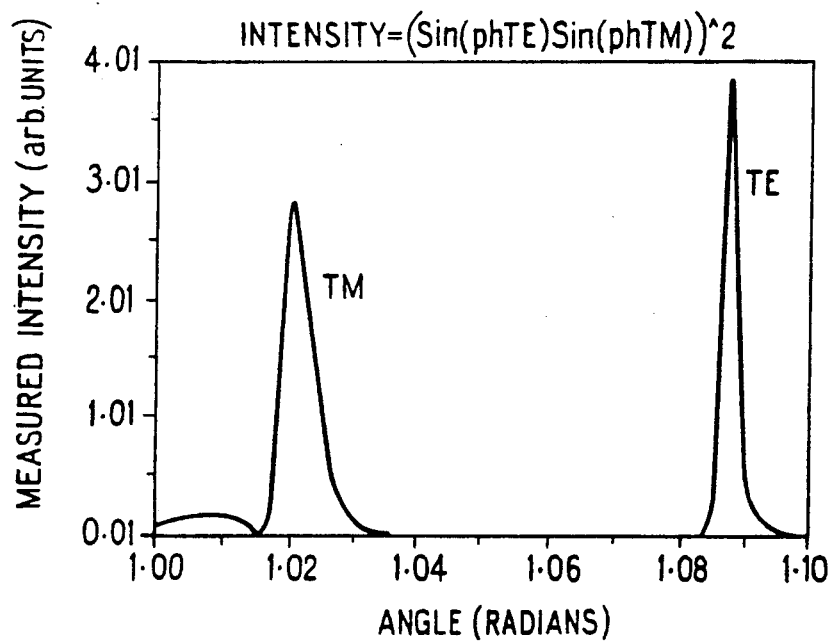
FIG. 3 is a graph of intensity signals for TE and TM components v angle derived for the above FIG. 2.

As with all SP and resonant mirror devices there is a resonance at some angle '0', at which a plane wave incident on the structure will produce a maximum intensity in the resonant film. This maximum will typically be many ($10^2+$) times the intensity produced at other angles of incidence. All the light is reflected for any angle of incidence, so the resonance is detected because of the effect on the phase of the reflected wave. See for example FIG. 2, showing the resonance and the resulting phase. Note that the width '$\Delta\theta$' is the same for both curves. Because the materials affect the electric component of the light wave differently from the magnetic component, the resonance occurs at different angles for the TE and TM input waves. Assuming the angular separation between TE and TM resonances is large compared with their angular width, as is normally the case, the phase of each component could be shown as in FIG. 2. The step height for either TE or TM as shown in FIG. 2 is $2\pi$. There may also be a 'background' phase difference between the curves at all angles 0 as shown in diagram 1 which is removed by the compensator. If this is done, remembering that a phase difference of $2\pi = 0$ (see FIG. 4), then a curve like FIG. 3 is obtained. This could also be described as $$\frac{1 - \text{Cos(Phase } TE - \text{Phase } TM)}{2}$$

The linearly polarized light produced by a polarizer 4 is reflected by a mirror 5 and thereafter focused by a cylindrical lens 6 on the device 1. The beam of light focused on the device is in the form of a wedge beam as shown in the drawing thus allowing a range of angles to be scanned simultaneously. The platform on which the prism 2 is mounted can be rotated so that the angles of incidence at which both components are coupled into the device can be adjusted. The prism is rotated so that the beam coupled into the device strikes the device at angles of incidence at which a resonance is excited for at least one of the TE and TM components. The prism may be rotated to a position where the resonance is excited for both of said TE and TM components.

A resonance mirror device consisting of a layer of zirconia, (refractive index, 1.84, thickness 620 A) on a layer of magnesium fluoride (refractive index, 1.38, thickness 7000 A) on a high index glass substrate (1.62) will have a typical resonance FWHM (Full Width Half Maximum) of about 6 arc minutes (TE resonance). This corresponds to a spectral width of 1.5 nm. Therefore a red LED (650 nm), with a Fabry-Perot etalon of optical length (refractive index × real length) 0.14 nm and finesse between 2 and say 20, giving a comb spectrum with a line spacing of 3 nm, would be a suitable source. With a band width of 50 nm, a total angular shift of up to ~ 3° may be measured, with a 12 arc minute resolution. This resolution corresponds to a change in sensing layer thickness of 50 A (with refractive index 1.5). The etalon may be formed using standard thin film deposition techniques. By using a broader source a wider angular range may be measured, but this range will be limited by the bandwidth of the compensating and analysing optics on the output side.

The reflected light from the device 1 is passed on to an analyser 6 and compensator 11 through an output optics including reflector 7 and a cylindrical lens 8. The analyser 11 is arranged at 90° to the polarizer. The two components are interfered at the analyser to allow the phase change on resonance to be detected. Off resonance both components undergo a similar phaseshift on total internal reflection and the relative phase between the components is adjusted by the compensator to give zero transmission through the analyser. This will apply for all angles except near resonance. Near resonance of either component, the phase shift between the TE and TM components will vary rapidly with angle, resulting in a maximum throughput of the analyser at resonance when all the light is transmitted. On rotating the analyser 90°, a series of dark lines or bands appears on a bright background. A polarizing beamsplitter may be used to give both bright and dark lines or bands. Due to the dispersive nature of the Resonant Mirror sensor, the angle at which resonance occurs varies with wavelength, resulting in an output beam which consists of a comb of lines for both TE+TM resonance each corresponding to the spectrum of the source (FIG. 5). Changes in the sensing layer cause the comb spectrum to be swept across the detector. As the angular spacing of the output spectrum is known, simply counting the number of maxima allows the shift in the angle to be measured. This counting system is very easily realized using simple digital electronics and results in only one data value to determine the resonance position. This gives advantages in speed and cost of the instrument.

The analyser 11 is arranged to receive the TE and TM components of light reflected from the device for producing an output beam having a spectrum including a series of bright and/or dark lines or bands corresponding to the lines or bands of the comb spectrum of the input beam of light as shown in FIGS. 5a and 5b. When a sensing layer of the resonant mirror device is sensitized by a test sample, there is an angular shift in the resonance angle, because of change in the angle of resonance. The series of lines or bands in the output spectrum are swept across a reference point as a result of the angular shift in the resonance angle. The series of lines or bands swept across the reference point are detected by a detector 12. Preferably the detector 12 is a silicon photodiode located at the reference point. The angular shift in the resonance angle is equal to the product of the counted number of lines or bands detected by the detector 12 and the distance between two adjacent lines or bands in the output spectrum. When a plurality of different test samples are tested simultaneously, by sensitizing different parts of the sensing range of the resonant mirror device, a linear detector is used in the path of the output beam for determining an angular shift corresponding to each of the test samples.

The compensator consists of two quarter wave plates which are manually adjusted to remove any phase difference which is introduced between the TE and TM components on total internal reflection and by birefringence in the optical path.

I claim:

1. A method of testing a biochemical sample, the method comprising providing an optical evanescent wave sensor device having a dielectric cavity and a sensing layer, providing an input beam of light having a comb spectrum with a uniform spacing between adjacent lines or bands of the spectrum, coupling said beam of light to said device to excite resonance in said device and projecting light reflected from said device onto an analyser for producing an output beam of light having a spectrum of a series of bright and/or dark lines or bands corresponding to the lines or bands of the comb spectrum of the input beam of light, sensitizing the sensing layer by the test sample, thereby causing an angular shift in the resonance angle, said lines or bands in the output spectrum being swept across a reference point as a result of said angular shift in the resonance angle and counting said lines or bands swept across said reference point, said angular shift in the resonance angle being equal to the product of the counted number of lines or bands swept across the reference point and the distance between two adjacent lines or bands in the output spectrum.

2. A method as claimed in claim 1, in which said beam of light has coherent TE and TM components and said device is arranged in the path of said input beam of light such that one of said components excites resonance in said device.

3. A method as claimed in claim 2, in which said device is arranged in the path of the input beam of light such that resonance is excited for both of said components.

4. A method as claimed in claims 2, in which said input beam of light is linearly polarized with TE and TM components by a polarizer arranged in the path of the input beam of light.

5. A method as claimed in claim 4, in which the polarizer is arranged at 45° to the TE and TM transmission axis for providing equal components of TE and TM light and the analyzer is arranged at 90° to the polarizer for providing said series of bright lines or bands in output spectrum.

6. A method as claimed in claim 2, in which a compensator is disposed adjacent said analyser to remove any off resonance phase difference which is introduced between the TE and TM components on total internal reflection and by birefringence in the device.

7. A method as claimed in claim 1, in which the sensor device is a resonant mirror device and a prism is disposed adjacent the mirror device for coupling light to the mirror device.

8. A method as claimed in claim 1, in which a detector is disposed at the reference point for detecting the lines or bands swept across the reference point.

9. A method as claimed in claim 8, in which said detector is a silicon photodiode.

10. A method as claimed in claim 1, in which an array of detectors is disposed in the path of said output beam to count lines or bands swept across two or more than two spaced reference points.

11. A method as claimed in claim 1, in which said input beam of light with comb spectrum is produced by a diode laser with multiple longitudinal modes.

12. A method as claimed in claim 1, in which said input beam of light with comb spectrum is produced by a broad band source such as a light emitting diode used in conjunction with Fahr-y-Perot or Mach-Zehnder interferometer.

13. An optical sensor for testing a biochemical sample, said sensor comprising means for providing an input beam of light having comb spectrum with a uniform spacing between adjacent lines or bands of the spectrum, an optical evanescent wave sensor device having a dielectric cavity and a sensing layer, weans for coupling said beam of light to said sensor device and projecting light reflected from said device onto an analyser for producing an output beam of light having a spectrum of a series of bright and/or dark lines or bands corresponding to the lines or bands of the comb spectrum of the input beam, said sensing layer being sensitized by the test sample, when the optical sensor is in use, thereby causing an angular shift in the resonance angle, said lines or bands in the output spectrum being swept across a reference point as a result of said angular shift in the resonance angle and means for counting said lines or bands swept across said reference point.

14. A sensor as claimed in claim 13, in which said input beam of light has coherent TE and TM components, and said sensor device is arranged in the path of said input beam of light such that one of said components excites resonance in said device.

15. A sensor as claimed in claim 14, in which said device is arranged in the path of the beam of light such that resonance is excited for both of said components.

16. A sensor as claimed in claim 15, including a lens arranged in the path of said beam of light for focusing the beam of light onto the device.

17. A sensor as claimed in claim 14, in which said beam of light is linearly polarized with TE and TM components by a polarizer arranged in the path of the input beam of light.

18. A sensor as claimed in claim 17, in which the polarizer is arranged at 45° to the TE and TM transmission axis, for providing equal components of TE and TM light and the analyser is arranged at 90° to the polarizer for providing said series of bright lines or bands.

19. A sensor as claimed in claim 13, in which said device is a resonant mirror device.

20. A sensor as claimed in claim 19, in which said coupling means is a prism.

21. A sensor as claimed in claim 20, in which said device is fabricated on a surface of said prism.

22. A sensor as claimed in claim 13, including a compensator disposed adjacent said analyser to remove any off resonance phase difference which is introduced between the TE and TM components on total internal reflection and by birefringence in the device.

23. A sensor as claimed in claim 13, in which a detector is disposed at the reference point for detecting the lines in the output spectrum swept across the reference point.

24. A sensor as claimed in claim 23, in which said detector is a photodiode.

25. A sensor as claimed in claim 13 including an array of detectors disposed in the path of said output beam to count lines swept across two or more than two spaced reference points.

26. A sensor as claimed in claim 13, in which said input beam of light having comb spectrum is produced by a diode laser with multiple longitudinal modes.

27. A sensor as claimed in claim 13, in which said input beam of light with comb spectrum is produced by a broad band source such as a light emitting diode used in conjunction with a Fahry-Perot or Mach-Zehnder interferometer.

* * * * *